US 7,838,702 B2
Nov. 23, 2010

(12) United States Patent
Van Laar et al.

(54) DIRECT AMINATION OF HYDROCARBONS

(75) Inventors: Frederik Van Laar, Dubai (AE); Ekkehard Schwab, Neustadt (DE); Joachim-Thierry Anders, Goennheim (DE); Sven Crone, Limburgerhof (DE); Karl Hoelemann, Mannheim (DE); Wolfgang Mackenroth, Tervuren (BE); Petr Kubanek, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/280,070

(22) PCT Filed: Feb. 13, 2007

(86) PCT No.: PCT/EP2007/051376

§ 371 (c)(1),
(2), (4) Date: Aug. 20, 2008

(87) PCT Pub. No.: WO2007/099028

PCT Pub. Date: Sep. 7, 2007

(65) Prior Publication Data

US 2009/0030234 A1   Jan. 29, 2009

(30) Foreign Application Priority Data

Feb. 24, 2006  (EP)  ................... 06110419

(51) Int. Cl.
*C07C 209/02* (2006.01)
*C07C 209/60* (2006.01)
(52) U.S. Cl. .................................... 564/408
(58) Field of Classification Search ............. 564/408
See application file for complete search history.

(56) References Cited

U.S. PATENT DOCUMENTS

| 2,948,755 | A | 8/1960 | Schmerling et al. |
| 3,919,155 | A | 11/1975 | Squire |
| 3,929,889 | A | 12/1975 | Squire |
| 4,001,260 | A | 1/1977 | DelPesco |
| 4,031,106 | A | 6/1977 | DelPesco |
| 6,204,411 | B1 | 3/2001 | Axon et al. |
| 6,281,387 | B1 | 8/2001 | Bhasin et al. |
| 2001/0044557 | A1 | 11/2001 | Bhasin et al. |
| 2008/0146846 | A1 | 6/2008 | Dialer et al. |
| 2009/0023956 | A1 | 1/2009 | van Laar et al. |
| 2009/0203941 | A1 | 8/2009 | Laar et al. |

FOREIGN PATENT DOCUMENTS

| CN | 1 424 304 | 6/2003 |
| CN | 1 458 140 | 11/2003 |
| CN | 1 555 921 | 12/2004 |
| DE | 196 34 110 | 2/1998 |
| WO | 99 10311 | 3/1999 |
| WO | 00 09473 | 2/2000 |
| WO | 00 69804 | 11/2000 |
| WO | 01 32600 | 5/2001 |
| WO | 2004 052833 | 6/2004 |
| WO | 2006 069673 | 7/2006 |
| WO | 2007 025882 | 3/2007 |

OTHER PUBLICATIONS

Wibaut, J., Berichte, vol. 50, pp. 541-546, (1917).

*Primary Examiner*—Brian J Davis
(74) *Attorney, Agent, or Firm*—Oblon, Spivak, McClelland, Maier & Neustadt, L.L.P.

(57) ABSTRACT

A process for aminating hydrocarbons with ammonia, wherein the $N_2$ content in the mixture at the reactor exit is less than 0.1% by volume based on the total volume of the mixture at the reactor exit.

23 Claims, No Drawings

DIRECT AMINATION OF HYDROCARBONS

The invention relates to a process for preferably continuously aminating, preferably directly aminating hydrocarbons, preferably by reacting hydrocarbons, more preferably aromatic hydrocarbons, in particular benzene, with ammonia, preferably in the presence of catalysts which catalyze the amination, the $N_2$ content in the mixture at the reactor exit being less than 0.1% by volume based on the total volume of the mixture at the reactor exit. The $N_2$ content in the mixture at the reactor outlet is preferably less than 100 ppm, most preferably less than 10 ppm. The expression "ppm" is understood to mean volume-ppm, which corresponds to mol-ppm assuming the ideal gas law. The present invention further provides processes for preferably continuously aminating, preferably directly aminating hydrocarbons, preferably by reacting hydrocarbons, more preferably aromatic hydrocarbons, especially benzene, with ammonia, preferably in the presence of catalysts which catalyze the amination, the amination being performed in the presence of at least two different catalysts (i) and (ii) which have a different activity for the amination, decomposition of ammonia and oxidation of hydrogen, preferably under identical conditions. In particular, the invention relates to processes for aminating hydrocarbons, preferably by reacting aromatic hydrocarbons, more preferably benzene, with ammonia, especially according to the following reaction, which is preferably catalyzed:

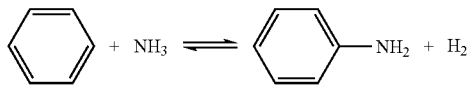

The invention further relates to processes for aminating hydrocarbons, preferably directly aminating hydrocarbons, more preferably aromatic hydrocarbons, especially benzene, with ammonia, the amination being performed in the presence of at least two different catalysts (i) and (ii), catalyst (ii), preferably under identical conditions, having a lower activity compared to catalyst (i) in decomposition of ammonia to hydrogen and nitrogen.

The commercial preparation of amines, especially of aromatic amines such as aniline, is typically carried out in multistage reactions. Aniline is prepared, for example, typically by converting benzene to a benzene derivative, for example nitrobenzene, chlorobenzene or phenol, and subsequently converting this derivative to aniline.

More advantageous than such indirect processes for preparing especially aromatic amines are methods which enable direct preparation of the amines from the corresponding hydrocarbons. A very elegant route is that of heterogeneously catalyzed direct amination of benzene, described for the first time in 1917 by Wibaut (Berichte, 50, 541-546). Since direct amination is equilibrium-limited, several systems have been described which shift the equilibrium limit by the selective removal of hydrogen from the reaction and enable increased benzene conversion. Most processes are based on the use of metal oxides which are reduced by hydrogen, hence removing the hydrogen from the reaction system and thus shifting the equilibrium.

CN 1555921A discloses the oxidoamination of benzene in the liquid phase, hydrogen peroxide functioning as the "O" donor. However, the use of $H_2O_2$ is suitable only to a limited extent for commodity chemicals owing to the cost and the low selectivity owing to subsequent reactions.

CA 553,988 discloses a process for preparing aniline from benzene, in which benzene, ammonia and gaseous oxygen are reacted over a platinum catalyst at a temperature of about 1000° C. Suitable platinum-comprising catalysts are platinum alone, platinum with certain specific metals and platinum together with certain specific metal oxides. In addition, CA 553,988 discloses a process for preparing aniline, in which benzene in the gas phase is reacted with ammonia in the presence of a reducible metal oxide at temperatures of from 100 to 1000° C., without addition of gaseous oxygen. Suitable reducible metal oxides are the oxides of iron, nickel, cobalt, tin, antimony, bismuth and copper.

U.S. Pat. No. 3,919,155 relates to the direct amination of aromatic hydrocarbons with ammonia, the catalyst used being nickel/nickel oxide which may additionally comprise oxides and carbonates of zirconium, strontium, barium, calcium, magnesium, zinc, iron, titanium, aluminum, silicon, cerium, thorium, uranium and alkali metals.

U.S. Pat. No. 3,929,889 likewise relates to the direct amination of aromatic hydrocarbons with ammonia over a nickel/nickel oxide catalyst, the catalyst used having been reduced partly to elemental nickel and subsequently reoxidized to obtain a catalyst which has a ratio of nickel:nickel oxide of from 0.001:1 to 10:1.

U.S. Pat. No. 4,001,260 discloses a process for directly aminating aromatic hydrocarbons with ammonia, a nickel/nickel oxide catalyst again being used, which has been applied to zirconium dioxide and has been reduced with ammonia before use in the amination reaction.

U.S. Pat. No. 4,031,106 relates in turn to the direct amination of aromatic hydrocarbons with ammonia over a nickel/nickel oxide catalyst on a zirconium dioxide support which also comprises an oxide selected from lanthanoids and rare earth metals.

DE 196 34 110 describes nonoxidative amination at a pressure of 10-500 bar and a temperature of 50-900° C., the reaction being effected in the presence of an acidic heterogeneous catalyst which has been modified with light and heavy platinum group metals.

WO 00/09473 describes a process for preparing amines by directly aminating aromatic hydrocarbons over a catalyst comprising at least one vanadium oxide.

WO 99/10311 teaches a process for directly aminating aromatic hydrocarbons at a temperature of <500° C. and a pressure of <10 bar. The catalyst used is a catalyst comprising at least one metal selected from transition metals, lanthanides and actinides, preferably Cu, Pt, V, Rh and Pd. To increase the selectivity and/or the conversion, preference is given to performing the direct amination in the presence of an oxidizing agent.

WO 00/69804 relates to a process for directly aminating aromatic hydrocarbons using, as a catalyst, a complex comprising a noble metal and a reducible metal oxide. Particular preference is given to catalysts comprising palladium and nickel oxide or palladium and cobalt oxide.

Indirect syntheses are also disclosed in CN 1424304, CN 1458140 and WO 2004/052833.

Most of the processes mentioned start from a mechanism for direct amination as detailed in the abstract of WO 00/69804. This is followed first by the (noble) metal-catalyzed preparation of the desired amine compound from the aromatic hydrocarbon and ammonia, and, in a second step, by the "scavenging" of the hydrogen formed in the first step with a reducible metal oxide. The same mechanistic considerations form the basis of the process in WO 00/09473, in which the hydrogen is scavenged with oxygen from vanadium oxides (page 1, lines 30 to 33). The same mechanism is also the basis of U.S. Pat. No. 4,001,260, as is evident from the remarks and the diagram in column 2, lines 16 to 44.

It is an object of the present invention to develop a particularly economically viable process for aminating hydrocarbons, in particular a process for reacting benzene with ammonia, in which a preferably continuous process is enabled with very high selectivity and/or very high conversion.

This object is achieved by the processes illustrated at the outset.

According to the technical teachings of the prior art, ammonia is decomposed significantly to hydrogen and nitrogen, for example with the nickel-nickel oxide systems. It has been found that, surprisingly, by virtue of the use of two catalysts (i) and (ii) which differ in their activity in the amination, decomposition of ammonia and oxidation of hydrogen the conversion to the aniline can be enhanced with the same selectivity. The use of the inventive catalyst system allows the decomposition of the ammonia to hydrogen and nitrogen to be reduced. At the same time, the lowering of the hydrogen concentration in the reaction mixture has a direct influence on the conversion to the aniline. While catalyst (i) compared to catalyst (ii) has a high activity in the amination, catalyst (ii) is notable for a high activity in the removal of hydrogen and low activity in the decomposition of ammonia to nitrogen and hydrogen. As a result of this combination of the catalysts, the benzene conversion to the aniline can be enhanced significantly. These advantages can be achieved in accordance with the present invention without the pressure having to be increased significantly.

Preference is therefore also given to processes in which the catalyst (ii) used is a compound which does not decompose ammonia to hydrogen and nitrogen until a temperature of at least 360° C., preferably at least 375° C., more preferably decomposes less than 0.2% by volume of the ammonia used. Particularly preferred catalysts (ii) are compounds which, at a temperature of 380° C., decompose at most 1%, in particular at most 0.8%, based on all of the ammonia in the reaction mixture, per one pass of the reaction mixture to hydrogen and nitrogen.

The different activity of catalysts (i) and (ii) with respect to the decomposition of ammonia can also be illustrated with reference to a temperature comparison. The temperature at which the activity of catalyst (ii) with respect to the decomposition of ammonia to hydrogen and nitrogen is equal to the activity of catalyst (i) with respect to the decomposition of ammonia to hydrogen and nitrogen is preferably at least 15 K, preferably at least 20 K, higher than the temperature at which catalyst (i), preferably under otherwise identical conditions, has the same activity with respect to the decomposition of ammonia to hydrogen and nitrogen.

Catalyst (ii) compared to catalyst (i) has a lower activity in decomposition of ammonia to hydrogen and nitrogen and hence higher overall efficiency in removal of hydrogen from the reaction mixture. In addition, in the course of temperature-programmed reduction with a hydrogen-comprising gas mixture in the temperature range from 50 to 250° C., catalyst (ii) preferably has a higher hydrogen uptake compared to catalyst (i) and the maximum of hydrogen consumption compared to catalyst (i) is additionally at a higher temperature, preferably at a temperature higher by at least 15 K.

Preference is therefore also given to processes in which the catalyst (ii) used is a compound which, in the temperature range between 50 and 250° C., has a higher hydrogen uptake, more preferably at least 1 mmol of hydrogen/g of catalyst higher, compared to catalyst (i). The hydrogen uptake is understood to mean the absolute consumption of hydrogen during the preferably temperature-programmed reduction of the catalyst in mmol of $H_2$ per g of catalyst. Preference is further given to processes in which catalysts (i) and (ii) are used for which the temperature within the temperature range between 50 and 250° C. at which the hydrogen uptake is at a maximum is higher for catalyst (ii) than for catalyst (i). At the same time, the maximum of the hydrogen uptake for catalyst (ii) within the temperature range between 50 and 250° C. is preferably at a temperature which is at least 15° C. higher than the temperature at which catalyst (i) has the maximum of the hydrogen uptake.

The catalysts used may be the catalysts known for the direct amination of hydrocarbons, especially those known for the direct amination of benzene with ammonia to give aniline. Catalyst (i) has the differences from catalyst (ii) illustrated at the outset, i.e. it is very active for the direct amination but leads to a decomposition of ammonia to hydrogen and nitrogen to a greater degree than catalyst (ii). Such catalysts have been described in a wide variety in the patent literature and are commonly known. Useful catalysts include, for example, customary metal catalysts, for example those based on nickel, iron, cobalt, copper, noble metals or alloys of these metals mentioned. Useful noble metals (NM) may include all noble metals, for example Ru, Rh, Pd, Ag, Ir, Pt and Au, the noble metals Ru and Rh preferably not being used alone but rather in alloy with other transition metals, for example Co, Cu, Fe and nickel or mixtures thereof. Such alloys are also used with preference in the case of use of the other noble metals; for example, supported NiCuNM; CoCuNM; NiCoCuNM, NiMoNM, NiCrNM, NiReNM, CoMoNM, CoCrNM, CoReNM, FeCuNM, FeCoCuNM, FeMoNM, FeReNM alloys are of interest, where NM is a noble metal, especially preferably Ag and/or Au.

Catalyst (i) may be used in generally customary form, for example as a powder or as a system usable in a fixed bed (for example extrudates, spheres, tablets, rings), in which case the catalytically active constituents may, if appropriate, be present on a support material. Useful support materials include, for example, inorganic oxides, for example $ZrO_2$, $SiO_2$, $Al_2O_3$, $TiO_2$, $B_2O_3$, $ThO_2$, $CeO_2$, $Y_2O_3$ and mixtures of these oxides, preferably $TiO_2$, $ZrO_2$, $Al_2O_3$ and $SiO_2$, more preferably $ZrO_2$. $ZrO_2$ is understood to mean either pure $ZrO_2$ or the normal Hf-comprising $ZrO_2$.

The catalysts used with preference in the process according to the invention may be regenerated, for example by passing a reductive atmosphere (for example $H_2$ atmosphere) over the catalyst or first an oxidative and then a reductive atmosphere over or through the catalyst bed.

Catalyst (i) may be present either in its reduced or oxidized form; catalyst (ii) is preferably present in its oxidized form.

The catalyst (i) used is preferably a compound which comprises one or more elements selected from the group of Ni, Cu, Fe, Co, preferably in combination with Mo or Ag, where the elements may each be present in reduced and/or oxidized form. Particularly preferred catalysts (i) are the combinations Co—Cu, Ni—Cu and/or Fe—Cu, especially the combinations thereof with an additional doping element Ni—Cu—X, Fe—Cu—X, Co—Cu—X where X is Ag or Mo. Especially preferred are alloys of NiCu(Ag or Mo) and/or FeCu(Ag or Mo).

In the catalyst (i), the proportion by weight of the elements Ni, Co and Fe together, i.e. the proportion of the total weight of these elements, not all elements necessarily being present in the catalyst, is preferably between 0.1% by weight and 75% by weight, more preferably between 1% by weight and 70% by weight, in particular between 2% by weight and 50% by weight, and the proportion by weight of Cu is between 0.1% by weight and 75% by weight, preferably between 0.1% by weight and 25% by weight, more preferably between 0.1% by weight and 20% by weight, in particular between 2.5% by weight and 10% by weight, based on the total weight of catalyst (i). In addition, catalyst (i) may comprise support material.

The proportion by weight of the doping element X in the total weight of catalyst (i) is preferably between 0.01% by weight and 8% by weight, more preferably between 0.1% by weight and 5% by weight, in particular between 0.5% by weight and 4% by weight. Catalyst (i) can preferably be activated before use in the process. Such an activation, which is preferably effected at a temperature between 200 and 600° C., more preferably at temperatures between 250 and 500° C., in particular at temperatures between 280 and 400° C., is preferably carried out with a mixture comprising inert gas and hydrogen or ammonia. The activation gas may also comprise further compounds. The activation reduces the metal oxides to the metal. The activation of catalyst (i) can preferably be carried out in the presence of catalyst (ii).

The catalyst (ii) used may be compounds which comprise Cu, Fe, Ni or mixtures thereof, which are supported on layered double hydroxides (LDH) or LDH-like compounds. Preference is given to using magnesium aluminum oxide, which is obtainable by calcining LDH or LDH-like compounds, as the support. A suitable process for preparing magnesium aluminum oxide, comprising the step of calcining LDH or LDH-like compounds, is disclosed, for example, in Catal. Today 1991, 11, 173 or in "Comprehensive Supramolecular Chemistry", (Ed. Alberti, Bein), Pergamon, N.Y., 1996, Vol 7, 251.

In the process according to the invention, the catalyst (ii) used is more preferably a compound which comprises one or more compounds selected from the group of Ni, Cu, Fe and Mo, and these elements may be present in one or more oxidation states, preferably on magnesium aluminum oxide as the support, more preferably NiO, CuO and/or $Fe_2O_3$ on magnesium aluminum oxide as the support. Especially preferred are NiO and/or CuO on magnesium aluminum oxide as the support.

As already illustrated, catalysts (i) and (ii) differ in their activities, especially in their activity to decompose ammonia to hydrogen and nitrogen. Catalyst (ii) preferably has a significantly lower activity to decompose ammonia and a high activity in removal of hydrogen from the reaction mixture. Catalyst (ii) preferably also catalyzes the reaction of benzene with ammonia to give aniline, albeit with a lower activity than catalyst (i). The catalyst (ii) used is preferably a compound which has a lower activity compared to catalyst (i) in decomposition of ammonia. Catalysts (i) and (ii) are thus preferably different; catalysts (i) and (ii) more preferably differ in terms of substance; catalyst (i) especially preferably comprises elements that catalyst (ii) does not comprise. Preference is given to using the two different catalysts (i) and (ii) in the process according to the invention; the different catalysts are more preferably already present at the start of the process in the reactor(s) in which the process is carried out.

The activity of the catalysts with regard to the decomposition of ammonia is preferably determined at temperatures between 50 and 600° C., the catalyst being heated at a heating rate of 2° C./min in a mixture of 5% by volume of $NH_3$ in argon and the concentration of ammonia, hydrogen and nitrogen in the offgas stream being monitored. The start of ammonia decomposition is preferably indicated by a nitrogen concentration in the offgas of greater than 50 ppm. The procedure can be effected in the sense of the temperature-programmed reduction.

It is possible with the amination process according to the invention to aminate any hydrocarbons, such as aromatic hydrocarbons, aliphatic hydrocarbons and cycloaliphatic hydrocarbons, which may have any substitution and may have heteroatoms and double or triple bonds within their chain or their ring/their rings. In the amination process according to the invention, preference is given to using aromatic hydrocarbons and heteroaromatic hydrocarbons. The particular products are the corresponding arylamines or heteroarylamines.

In the context of the present invention, an aromatic hydrocarbon is understood to mean an unsaturated cyclic hydrocarbon which has one or more rings and comprises exclusively aromatic C—H bonds. The aromatic hydrocarbon preferably has one or more 5- or 6-membered rings.

A heteroaromatic hydrocarbon is understood to mean those aromatic hydrocarbons in which one or more of the carbon atoms of the aromatic ring is/are replaced by a heteroatom selected from N, O and S.

The aromatic hydrocarbons or the heteroaromatic hydrocarbons may be substituted or unsubstituted. A substituted aromatic or heteroaromatic hydrocarbon is understood to mean compounds in which one or more hydrogen atoms which is/are bonded to a carbon atom or heteroatom of the aromatic ring is/are replaced by another radical. Such radicals are, for example, substituted or unsubstituted alkyl, alkenyl, alkynyl, heteroalkyl, heteroalkenyl, heteroalkynyl, cycloalkyl and/or cycloalkynyl radicals. In addition, the following radicals are possible: halogen, hydroxyl, alkoxy, aryloxy, amino, amido, thio and phosphino. Preferred radicals of the aromatic or heteroaromatic hydrocarbons are selected from $C_{1-6}$-alkyl, $C_{1-6}$-alkenyl, $C_{1-6}$-alkynyl, $C_{3-8}$-cycloalkyl, $C_{3-8}$-cycloalkenyl, alkoxy, aryloxy, amino and amido, where $C_{1-6}$ relates to the number of carbon atoms in the main chain of the alkyl radical, of the alkenyl radical or of the alkynyl radical, and $C_{3-8}$ to the number of carbon atoms of the cycloalkyl or cycloalkenyl ring. It is also possible that the substituents (radicals) of the substituted aromatic or heteroaromatic hydrocarbon have further substituents.

The number of substituents (radicals) of the aromatic or heteroaromatic hydrocarbon is arbitrary. In a preferred embodiment, the aromatic or heteroaromatic hydrocarbon has, however, at least one hydrogen atom which is bonded directly to a carbon atom or a heteroatom of the aromatic ring. Thus, a 6-membered ring preferably has 5 or fewer substituents (radicals) and a 5-membered ring preferably has 4 or fewer substituents (radicals). A 6-membered aromatic or heteroaromatic ring more preferably bears 4 or fewer substituents, even more preferably 3 or fewer substituents (radicals). A 5-membered aromatic or heteroaromatic ring preferably bears 3 or fewer radicals, more preferably 2 or fewer radicals.

In a particularly preferred embodiment of the process according to the invention, an aromatic or heteroaromatic hydrocarbon of the general formula

is used, where the symbols are each defined as follows:
A is independently aryl or heteroaryl, A is preferably selected from phenyl, diphenyl, diphenylmethane, benzyl, dibenzyl, naphthyl, anthracene, pyridyl and quinoline;
n is from 0 to 5, preferably from 0 to 4, especially in the case when A is a 6-membered aryl or heteroaryl ring; in the case that A is a 5-membered aryl or heteroaryl ring, n is preferably from 0 to 4; irrespective of the ring size, n is more preferably from 0 to 3, most preferably from 0 to 2 and in particular from 0 to 1; the remaining hydrocarbon atoms or heteroatoms of A which do not bear any substituents B bear hydrogen atoms, or, if appropriate, no substituents;

B is independently selected from the group consisting of alkyl, alkenyl, alkynyl, substituted alkyl, substituted alkenyl, substituted alkynyl, heteroalkyl, substituted heteroalkyl, heteroalkenyl, substituted heteroalkenyl, heteroalkynyl, substituted heteroalkynyl, cycloalkyl, cycloalkenyl, substituted cycloalkyl, substituted cycloalkenyl, halogen, hydroxy, alkoxy, aryloxy, carbonyl, amino, amido, thio and phosphino; B is preferably independently selected from $C_{1-6}$-alkyl, $C_{1-6}$-alkenyl, $C_{1-6}$-alkynyl, $C_{3-8}$-cycloalkyl, $C_{3-8}$-cycloalkenyl, alkoxy, aryloxy, amino and amido.

The term "independently" means that, when n is 2 or greater, the substituents B may be identical or different radicals from the groups mentioned.

In the present application, alkyl is understood to mean branched or unbranched, saturated acyclic hydrocarbyl radicals. Examples of suitable alkyl radicals are methyl, ethyl, n-propyl, i-propyl, n-butyl, t-butyl, i-butyl, etc. The alkyl radicals used preferably have from 1 to 50 carbon atoms, more preferably from 1 to 20 carbon atoms, even more preferably from 1 to 6 carbon atoms and in particular from 1 to 3 carbon atoms.

In the present application, alkenyl is understood to mean branched or unbranched, acyclic hydrocarbyl radicals which have at least one carbon-carbon double bond. Suitable alkenyl radicals are, for example, 2-propenyl, vinyl, etc. The alkenyl radicals have preferably from 2 to 50 carbon atoms, more preferably from 2 to 20 carbon atoms, even more preferably from 2 to 6 carbon atoms and in particular from 2 to 3 carbon atoms. The term alkenyl also encompasses radicals which have either a cis-orientation or a trans-orientation (alternatively E or Z orientation).

In the present application, alkynyl is understood to mean branched or unbranched, acyclic hydrocarbyl radicals which have at least one carbon-carbon triple bond. The alkynyl radicals preferably have from 2 to 50 carbon atoms, more preferably from 2 to 20 carbon atoms, even more preferably from 1 to 6 carbon atoms and in particular from 2 to 3 carbon atoms.

Substituted alkyl, substituted alkenyl and substituted alkynyl are understood to mean alkyl, alkenyl and alkynyl radicals in which one or more hydrogen atoms which are bonded to one carbon atom of these radicals are replaced by another group. Examples of such other groups are heteroatoms, halogen, aryl, substituted aryl, cycloalkyl, cycloalkenyl, substituted cycloalkyl, substituted cycloalkenyl and combinations thereof. Examples of suitable substituted alkyl radicals are benzyl, trifluoromethyl, inter alia.

The terms heteroalkyl, heteroalkenyl and heteroalkynyl are understood to mean alkyl, alkenyl and alkynyl radicals in which one or more of the carbon atoms in the carbon chain is replaced by a heteroatom selected from N, O and S. The bond between the heteroatom and a further carbon atom may be saturated, or, if appropriate, unsaturated.

In the present application, cycloalkyl is understood to mean saturated cyclic nonaromatic hydrocarbyl radicals which are composed of a single ring or a plurality of fused rings. Suitable cycloalkyl radicals are, for example, cyclopentyl, cyclohexyl, cyclooctanyl, bicyclooctyl, etc. The cycloalkyl radicals have preferably between 3 and 50 carbon atoms, more preferably between 3 and 20 carbon atoms, even more preferably between 3 and 8 carbon atoms and in particular between 3 and 6 carbon atoms.

In the present application, cycloalkenyl is understood to mean partly unsaturated, cyclic nonaromatic hydrocarbyl radicals which have a single fused ring or a plurality of fused rings. Suitable cycloalkenyl radicals are, for example, cyclopentenyl, cyclohexenyl, cyclooctenyl, etc. The cycloalkenyl radicals have preferably from 3 to 50 carbon atoms, more preferably from 3 to 20 carbon atoms, even more preferably from 3 to 8 carbon atoms and in particular from 3 to 6 carbon atoms.

Substituted cycloalkyl and substituted cycloalkenyl radicals are cycloalkyl and cycloalkenyl radicals, in which one or more hydrogen atoms of any carbon atom of the carbon ring is replaced by another group. Such other groups are, for example, halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cyclo-alkenyl, an aliphatic heterocyclic radical, a substituted aliphatic heterocyclic radical, heteroaryl, substituted heteroaryl, alkoxy, aryloxy, boryl, phosphino, amino, silyl, thio, seleno and combinations thereof. Examples of substituted cycloalkyl and cycloalkenyl radicals are 4-dimethylaminocyclohexyl, 4,5-dibromocyclohept-4-enyl, inter alia.

In the context of the present application, aryl is understood to mean aromatic radicals which have a single aromatic ring or a plurality of aromatic rings which are fused, joined via a covalent bond or joined by a suitable unit, for example a methylene or ethylene unit. Such suitable units may also be carbonyl units, as in benzophenol, or oxygen units, as in diphenyl ether, or nitrogen units, as in diphenylamine. The aromatic ring or the aromatic rings are, for example, phenyl, naphthyl, diphenyl, diphenyl ether, diphenylamine and benzophenone. The aryl radicals preferably have from 6 to 50 carbon atoms, more preferably from 6 to 20 carbon atoms, most preferably from 6 to 8 carbon atoms.

Substituted aryl radicals are aryl radicals in which one or more hydrogen atoms which are bonded to carbon atoms of the aryl radical are replaced by one or more other groups. Suitable other groups are alkyl, alkenyl, alkynyl, substituted alkyl, substituted alkenyl, substituted alkynyl, cycloalkyl, cycloalkenyl, substituted cycloalkyl, substituted cycloalkenyl, heterocyclo, substituted heterocyclo, halogen, halogen-substituted alkyl (e.g. $CF_3$), hydroxyl, amino, phosphino, alkoxy, thio and both saturated and unsaturated cyclic hydrocarbons which may be fused on the aromatic ring or on the aromatic rings or may be joined by a bond, or may be joined to one another via a suitable group. Suitable groups have already been mentioned above.

According to the present application, heterocyclo is understood to mean a saturated, partly unsaturated or unsaturated, cyclic radical in which one or more carbon atoms of the radical are replaced by a heteroatom, for example N, O or S. Examples of heterocyclo radicals are piperazinyl, morpholinyl, tetrahydropyranyl, tetrahydrofuranyl, piperidinyl, pyrrolidinyl, oxazolinyl, pyridyl, pyrazyl, pyridazyl, pyrimidyl.

Substituted heterocyclo radicals are those heterocyclo radicals in which one or more hydrogen atoms which are bonded to one of the ring atoms are replaced by another group. Suitable other groups are halogen, alkyl, substituted alkyl, aryl, substituted aryl, heteroaryl, substituted heteroaryl, alkoxy, aryloxy, boryl, phosphino, amino, silyl, thio, seleno and combinations thereof.

Alkoxy radicals are understood to mean radicals of the general formula —$OZ^1$ in which $Z^1$ is selected from alkyl, substituted alkyl, cycloalkyl, substituted cycloalkyl, heterocycloalkyl, substituted heterocycloalkyl, silyl and combinations thereof. Suitable alkoxy radicals are, for example, methoxy, ethoxy, benzyloxy, t-butoxy, etc. The term aryloxy is understood to mean those radicals of the general formula —$OZ^1$ in which $Z^1$ is selected from aryl, substituted aryl, heteroaryl, substituted heteroaryl and combinations thereof.

Suitable aryloxy radicals are phenoxy, substituted phenoxy, 2-pyridinoxy, 8-quinolinoxy, inter alia.

Amino radicals are understood to mean radicals of the general formula —$NZ^1Z^2$ in which $Z^1$ and $Z^2$ are each independently selected from hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

Aromatic or heteroaromatic hydrocarbons used with preference in the amination process according to the invention are selected from benzene, diphenylmethane, naphthalene, anthracene, toluene, xylene, phenol and aniline, and also pyridine, pyrazine, pyridazine, pyrimidine and quinoline. It is also possible to use mixtures of the aromatic or heteroaromatic hydrocarbons mentioned. Particular preference is given to using the aromatic hydrocarbons, benzene, naphthalene, anthracene, toluene, xylene, pyridine, phenol and aniline, very particular preference to using benzene, toluene and pyridine.

Especially preferably, benzene is used in the amination process according to the invention, so that the product formed is aniline.

The compound through which the amino group is introduced is more preferably ammonia. This means that, in accordance with the invention, the hydrocarbons, especially the benzene, are more preferably reacted with ammonia. If appropriate, compounds which eliminate ammonia under the reaction conditions may also find use. For the preparation of mono- and dialkyl-N,(N)-substituted aromatic amines, for example mono- and/or dimethylaniline, it is also possible to use mono- and dialkylamines, preferably mono- and di(m) ethylamine.

The reaction conditions in the amination processes according to the invention are dependent upon factors including the aromatic hydrocarbon to be aminated and the catalyst used.

The amination, preferably the amination of benzene, i.e. the reaction of benzene with ammonia, is effected generally at temperatures of from 200 to 800° C., preferably from 300 to 700° C., more preferably from 325 to 600° C. and most preferably from 350 to 500° C.

The reaction pressure in the amination, preferably in the amination of benzene, i.e. the reaction of benzene with ammonia, is preferably from 1 to 900 bar, more preferably from 1 to 300 bar, in particular from 5 to 125 bar, especially preferably from 15 to 110 bar.

The residence time in the amination process according to the invention, preferably in the amination of benzene, is generally from 15 minutes to 8 hours, preferably from 15 minutes to 4 hours, more preferably from 15 minutes to 1 hour, in the case of performance in a batchwise process. In the case of performance in a preferred continuous process, the residence time is generally from 0.1 second to 20 minutes, preferably from 0.5 second to 10 minutes. For the preferred continuous processes, "residence time" in this context means the residence time over the catalyst, hence the residence time in the catalyst bed for fixed bed catalyst; for fluidized bed reactors, the synthesis part of the reactor (part of the reactor where the catalyst is localized) is considered.

The relative amount of the hydrocarbon used and of the amine component is dependent upon the amination reaction carried out and the reaction conditions. In general, at least stoichiometric amounts of the hydrocarbon and the amine component are used. However, it is typically preferred to use one of the reaction partners in a stoichiometric excess in order to achieve a shift in the equilibrium to the side of the desired product and hence a higher conversion. Preference is given to using the amine component in a stoichiometric excess.

The amination process according to the invention may be carried out continuously, batchwise or semicontinuously. Suitable reactors are thus both stirred tank reactors and tubular reactors. Typically reactors are, for example, high pressure stirred tank reactors, autoclaves, fixed bed reactors, fluidized bed reactors, moving beds, circulating fluidized beds, salt bath reactors, plate heat exchangers as reactors, tray reactors having a plurality of trays with or without heat exchange or drawing/feeding of substreams between the trays, in possible designs as radial flow or axial flow reactors, continuous stirred tanks, bubble reactors, etc., and the reactor suitable in each case for the desired reaction conditions (such as temperature, pressure and residence time) is used. The reactors may each be used as a single reactor, as a series of individual reactors and/or in the form of two or more parallel reactors. The reactors may be operated in an AB mode (alternating mode). The process according to the invention may be carried out as a batch reaction, semicontinuous reaction or continuous reaction. The specific reactor construction and performance of the reaction may vary depending on the amination process to be carried out, the state of matter of the aromatic hydrocarbon to be aminated, the required reaction times and the nature of the nitrogen-containing catalyst used. Preference is given to carrying out the process according to the invention for direct amination in a high pressure stirred tank reactor, fixed bed reactor or fluidized bed reactor.

In a particularly preferred embodiment, one or more fixed bed reactors are used in the amination of benzene to aniline.

The hydrocarbon and the amine component may be introduced in gaseous or liquid form into the reaction zone of the particular reactor. The preferred phase is dependent in each case upon the amination carried out and the reactor used. In a preferred embodiment, for example in the preparation of aniline from benzene, benzene and ammonia are preferably present as gaseous reactants in the reaction zone. Typically, benzene is fed as a liquid which is heated and evaporated to form a gas, while ammonia is present either in gaseous form or in a supercritical phase in the reaction zone. It is likewise possible that benzene is present in a supercritical phase at least together with ammonia.

The hydrocarbon and the amine component may be introduced together into the reaction zone of the reactor, for example as a premixed reactant stream, or separately. In the case of a separate addition, the hydrocarbon and the amine component may be introduced simultaneously, offset in time or successively into the reaction zone of the reactor. Preference is given to adding the amine component and adding the hydrocarbon offset in time.

If appropriate, further coreactants, cocatalysts or further reagents are introduced into the reaction zone of the reactor in the process according to the invention, depending in each case on the amination carried out. For example, in the amination of benzene, oxygen or an oxygen-comprising gas may be introduced into the reaction zone of the reactor as a coreactant. The relative amount of gaseous oxygen which can be introduced into the reaction zone is variable and depends upon factors including the catalyst system used. The molar ratio of gaseous oxygen to aniline may, for example, be in the range from 0.05:1 to 1:1, preferably from 0.1:1 to 0.5:1. However, it is also possible to perform the amination of benzene without addition of oxygen or an oxygen-comprising gas into the reaction zone.

Preference is given to processes in which the weight ratio of the two different catalysts (i) and (ii) varies in the course of the amination. Preference is further given to a structured arrangement of catalysts (i) and (ii), since this structured arrangement allows higher conversions of benzene to aniline to be achieved compared to the use of separate catalysts (i) or (ii).

Preference is also given to a layered structure, preferably with at least 4 layers, in which case catalysts (i) and (ii) are arranged in alternation, i.e. one layer comprising catalyst 1 is followed by a layer comprising catalyst 2, then again by a layer comprising catalyst 1, then by a layer comprising catalyst 2, etc.

Very particular preference is further given to a structure of the catalysts in which the amination takes place first in a zone comprising catalyst (i) and the content of catalyst (ii) rises further on. The rise in catalyst (ii) in the reaction zone may be constant and/or in stages, and rise in a linear or greater than proportional manner. Such a structured arrangement allows hydrogen to be increasingly removed from the equilibrium and thus the benzene conversion to be increased. Preference is given to processes in which the content of catalyst (ii) in the reaction zone rises in a linear manner.

The structured arrangement may preferably have such an appearance that first a zone with 100% catalyst (i), then a zone of 75% catalyst (i) and 25% catalyst (ii), then a zone with 50% catalyst (i) and 50% catalyst (ii), then a zone of 25% catalyst (i) and 75% catalyst (ii) and then a zone of 100% catalyst (ii) is used.

The amination can be performed preferably at a molar ratio of ammonia to hydrocarbon of at least 1.

After the amination, the desired product can be isolated by processes known to those skilled in the art.

EXAMPLES

Example 1

Preparation of Catalyst (i)

The catalyst is prepared in accordance with DE-A 44 28 004:

An aqueous solution of nickel nitrate, copper nitrate and zirconium acetate which comprises 4.48% by weight of Ni (calculated as NiO), 1.52% by weight of Cu (calculated as CuO) and 2.28% by weight of Zr (calculated as $ZrO_2$) is precipitated simultaneously in a stirrer vessel in a constant stream with a 20% aqueous sodium carbonate solution at a temperature of 70° C., in such a way that the pH of 7.0 measured with a glass electrode is maintained. The resulting suspension is filtered and the filtercake is washed with mineralized water until the electrical conductivity of the filtrate is approx. 20 µs. Sufficient ammonium heptamolybdate is then incorporated into the still-moist filtercake that the oxide mixture specified below is obtained. Thereafter, the filtercake is dried at a temperature of 150° C. in a drying cabinet or a spray dryer. The hydroxide-carbonate mixture obtained in this way is then heat-treated at a temperature of from 430 to 460° C. over a period of 4 hours. The oxidic species thus prepared has the composition: 50% by weight of NiO, 17% by weight of CuO, 1.5% by weight of $MoO_3$ and 31.5% by weight of $ZrO_2$. In the course of heating in a gas stream comprising hydrogen in the temperature range from 50 to 250° C., the catalyst has a hydrogen uptake of 1.07 mmol of hydrogen/g of catalyst and the maximum of hydrogen consumption is at a temperature of 140° C.

Example 2

Preparation of Catalyst (ii)

An aqueous solution of nickel nitrate, copper nitrate, magnesium nitrate and aluminum nitrate which comprises 8.1 kg of NiO, 2.9 kg of CuO, 2.8 kg of MgO and 10.2 kg of $Al_2O_3$ in 111 kg of total solution is precipitated simultaneously in a stirred vessel in a constant stream with an aqueous solution of 7.75 kg of sodium carbonate and 78 kg of sodium hydroxide in a total volume of 244 liters at a temperature of 20° C., in such a way that the pH of 9.5 measured with a glass electrode is maintained. The resultant suspension is filtered and the filtercake is washed with the demineralized water until the electrical conductivity of the filtrate is approx. 20 µs. Thereafter, the filtercake is dried in a drying cabinet at a temperature of 150° C. The hydroxide-carbonate mixture obtained in this way is then heat-treated at a temperature of from 430 to 460° C. over a period of 4 hours. The oxidic species thus prepared has the composition: 56.6% by weight of NiO, 19.6% by weight of CuO, 15.4% by weight of MgO and 8.5% by weight of $Al_2O_3$. In the course of heating in a gas stream comprising hydrogen in the temperature range from 50 to 250° C., the catalyst has a hydrogen uptake of 2.41 mmol of hydrogen/g of catalyst and the maximum of hydrogen consumption is at a temperature of 159° C.

Example 3

Temperature-programmed Reduction of the Catalyst in Ammonia 100 mg of catalyst powder are heated in a 30 ml/min gas stream of 5% by volume of ammonia in argon with a heating rate of 2° C. per minute. The concentration of ammonia, hydrogen and nitrogen in reaction gas downstream of the catalyst bed was monitored by means of mass spectroscopy. Ammonia is converted at a nitrogen concentration higher than 50 ppm. The values for the two catalysts (i) and (ii) can be taken from the table.

| Catalyst (i) | | Catalyst (ii) | |
| --- | --- | --- | --- |
| Temperature (° C.) | Ammonia conversion (%) | Temperature (° C.) | Ammonia conversion (%) |
| 330 | 0.00 | 330 | 0.00 |
| 340 | 0.00 | 340 | 0.00 |
| 350 | 0.00 | 350 | 0.00 |
| 360 | 0.98 | 360 | 0.00 |
| 370 | 3.73 | 370 | 0.00 |
| 380 | 7.45 | 380 | 0.79 |
| 390 | 12.13 | 390 | 1.86 |
| 400 | 18.57 | 400 | 2.2 |

Example 4

Amination of Benzene on Pure Catalyst (i)

220 ml of catalyst (i) in the form of 6×3 mm tablets are heated to 350° C. in a tubular reactor. At the total pressure of 40 bar, 156 g/hour of benzene and 306 g/ammonia are supplied to the catalyst. The effluent from the reactor is cooled at a temperature below 10° C. and the organic phase of the condensate is analyzed by means of gas chromatography. The content of aniline in % by weight averaged through 5 hours is 2.91% and the space-time yield is 9.56 g of aniline/kg of catalyst (i) per hour.

Example 5

Amination of Benzene on Pure Catalyst (ii)

220 ml of catalyst (ii) in the form of 6×3 mm tablets are heated to 350° C. in a tubular reactor. At the total pressure of 40 bar, 156 g/hour of benzene and 306 g/ammonia are supplied to the catalyst. The effluent from the reactor is cooled at a temperature below 10° C. and the organic phase of the condensate is analyzed by means of gas chromatography. The content of aniline in % by weight averaged through 5 hours is 1.77% and the space-time yield is 8.64 g of aniline/kg of catalyst (ii) per hour.

Example 6 (Inventive)

Amination on a Structured Mixture of Catalyst (i) and Catalyst (ii)

220 ml of catalyst (i) in the form of 6×3 mm tablets are installed together with 220 ml of catalyst (ii) in the form of 6×3 mm tablets in a tubular reactor. In the first zone, 50 ml of catalyst (i) are installed, followed by a zone comprising 112 ml of catalyst (i) and 57 ml of catalyst (ii) mixed homogeneously, then by a zone comprising 57 ml of catalyst (i) and 114 ml of catalyst (ii) mixed homogeneously and then a zone comprising 50 ml of catalyst (ii). The reactor is heated to 350° C., then the reaction mixture is supplied. At the total pressure of 40 bar, 156 g/hour of benzene and 306 g/ammonia are supplied to the catalyst. The effluent from the reactor is cooled at a temperature below 10° C. and the organic phase of the condensate is analyzed by means of gas chromatography. The content of aniline in % by weight averaged through 5 hours is 6.08% and the space-time yield is 11.56 g of aniline per kg of catalyst bed and hour.

What is claimed is:

1. A process for aminating aromatic hydrocarbons with ammonia, which comprises performing the amination in the presence of at least two different catalysts (i) and (ii) which have different activities for the amination, the decomposition of ammonia and the oxidation of hydrogen.

2. A process for aminating aromatic hydrocarbons with ammonia, which comprises performing the amination in the presence of at least two different catalysts (i) and (ii), catalyst (ii) having a lower activity compared to catalyst (i) in decomposition of ammonia to hydrogen and nitrogen.

3. The process according to claim 1, wherein the temperature at which the activity of catalyst (ii) with respect to the decomposition of ammonia to hydrogen and nitrogen is equal to the activity of catalyst (i) with respect to the decomposition of ammonia to hydrogen and nitrogen is at least 15 K higher than the temperature at which catalyst (i), under otherwise identical conditions, has the same activity with respect to the decomposition of ammonia to hydrogen and nitrogen.

4. The process according to claim 1, wherein the catalyst (ii) is a compound which does not decompose ammonia to hydrogen and nitrogen until a temperature of at least 360° C. is reached.

5. The process according to claim 1, wherein the catalyst (ii) is a compound which, at a temperature of 380° C., decomposes at most 1% of ammonia to hydrogen and nitrogen.

6. The process according to claim 1, wherein the catalyst (ii) is a compound which, in the temperature range between 50 and 250° C., has a higher hydrogen uptake compared to catalyst (i).

7. The process according to claim 1, wherein the temperature within the temperature range between 50 and 250° C. at which the hydrogen uptake is at a maximum is higher for catalyst (ii) than for catalyst (i).

8. The process according to claim 7, wherein the maximum of the hydrogen uptake for catalyst (ii) within the temperature range between 50 and 250° C. is at a temperature which is at least 15° C. higher than the temperature at which catalyst (i) has the maximum of the hydrogen uptake.

9. The process according to claim 1, wherein catalyst (i) is activated before use in the process.

10. The process according to claim 9, wherein the activation is carried out at a temperature between 200 and 600° C.

11. The process according to claim 9, wherein the activation of the catalyst (i) is carried out with a mixture comprising hydrogen or ammonia and, optionally, inert gas.

12. The process according to claim 9, wherein the activation of catalyst (i) is carried out in the presence of catalyst (ii).

13. The process according to claim 1, wherein the catalyst (i) is a compound which comprises one or more elements selected from the group consisting of Ni, Cu, Fe and Co, and the elements may each be present in reduced and/or oxidized form.

14. The process according to claim 1, wherein the catalyst (ii) is a compound which comprises one or more compounds selected from the group consisting of Ni, Cu, Fe and Mo, and these elements may be present in one or more oxidation states.

15. The process according to claim 1, wherein the weight ratio of the two different catalysts varies during the course of the amination.

16. The process according to claim 15, wherein the content of catalyst (ii) in the reaction zone rises constantly and/or in stages, in a linear or greater than proportional manner.

17. The process according to claim 16, wherein the content of catalyst (ii) in the reaction zone rises in a linear manner.

18. The process according to claim 1, wherein the amination is performed continuously.

19. The process according to claim 1, wherein the amination is performed at temperatures between 200 and 800° C.

20. The process according to claim 1, wherein the amination is performed at pressures between 1 and 900 bar.

21. The process according to claim 1, wherein the amination is performed at a molar ratio of ammonia to hydrocarbon of at least 1.

22. The process according to claim 1, wherein the $N_2$ content in the mixture at the reactor exit is less than 0.1% by volume based on the total volume of the mixture at the reactor exit.

23. The process according to claim 2, wherein the $N_2$ content in the mixture at the reactor exit is less than 0.1% by volume based on the total volume of the mixture at the reactor exit.

* * * * *